United States Patent

Baffelli et al.

[11] Patent Number: 5,743,738
[45] Date of Patent: Apr. 28, 1998

[54] INTERDENTAL WEDGE

[75] Inventors: Gianni Baffelli, Tesserete; Beat A. Von Weissenfluh, Gentilino; Beat Kilcher, Bosco Luganese, all of Switzerland

[73] Assignee: Hawe Neos Dental, Bioggio, Switzerland

[21] Appl. No.: 669,958

[22] Filed: Jun. 25, 1996

[30] Foreign Application Priority Data

Jun. 28, 1995 [CH] Switzerland .......................... 01892/95

[51] Int. Cl.$^6$ .................................................... A61C 7/00
[52] U.S. Cl. ............................................................ 433/149
[58] Field of Search ...................................... 433/149, 39

[56] References Cited

U.S. PATENT DOCUMENTS

| | | | |
|---|---|---|---|
| 2,867,905 | 1/1959 | Meacham | 433/149 |
| 4,337,041 | 6/1982 | Harsany | 433/149 |
| 4,468,199 | 8/1984 | Weikel | 433/149 |
| 4,631,030 | 12/1986 | Von Weissenfluh | 433/149 |
| 5,421,725 | 6/1995 | Von Weissenfluh | 433/149 |
| 5,527,181 | 6/1996 | Rawls et al. | 433/149 |

FOREIGN PATENT DOCUMENTS

| | | |
|---|---|---|
| 0169803 | 1/1986 | European Pat. Off. . |
| 0594535 | 4/1994 | European Pat. Off. . |
| 0668060 | 8/1995 | European Pat. Off. . |
| 8912620 | 1/1990 | Germany . |

*Primary Examiner*—Cary E. O'Connor
*Attorney, Agent, or Firm*—Foley & Lardner

[57] ABSTRACT

The interdental wedge for the use during the insertion of approximal fillings of light curing synthetic material comprises the combination of a sole portion having disposed thereon an insert of a light conducting synthetic material and a light conducting element, such as a light reflector, to conduct the light necessary for curing and coming from the front surface of the wedge on the filling. The sole portion consists of a material which is compressible and requires strongly increasing forces for further compression; thus, the wedge can snugly fit to the approximal contour of the tooth to be treated and exert sufficiently high separation forces. Preferably, the material of the sole portion is wood whose fibers are preferably aligned in lengthwise direction of the wedge, and/or a synthetic material having included therein compressible filler particles. Thermoplastics and thermoplastic elastomers are preferred synthetic materials.

Such a wedge combines the advantages of wood or a synthetic material having similar compression characteristics for a good adhesion of the wedge and sufficient separating forces, with the advantages of a wedge made of a light conducting synthetic material, in order to bring about or to accelerate the curing of the synthetic filling.

24 Claims, 4 Drawing Sheets

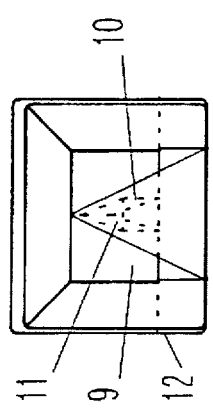
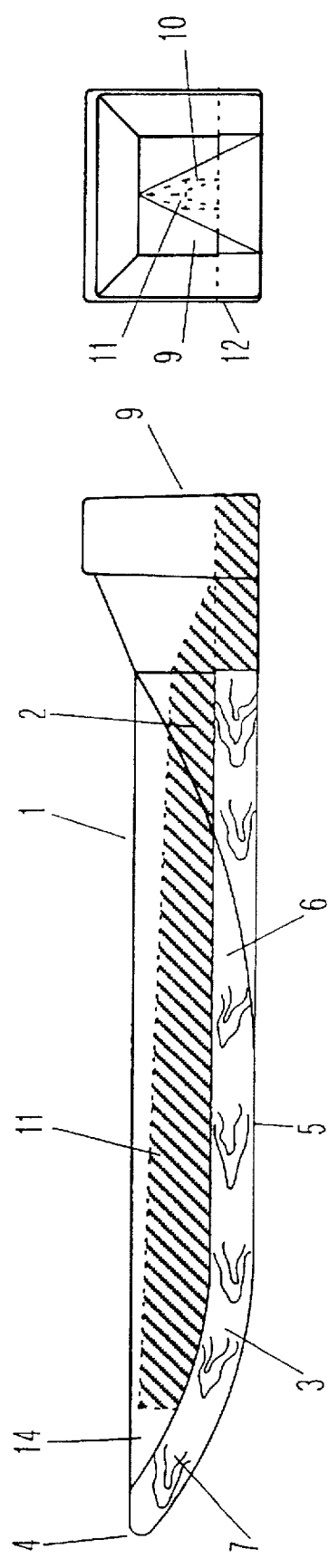
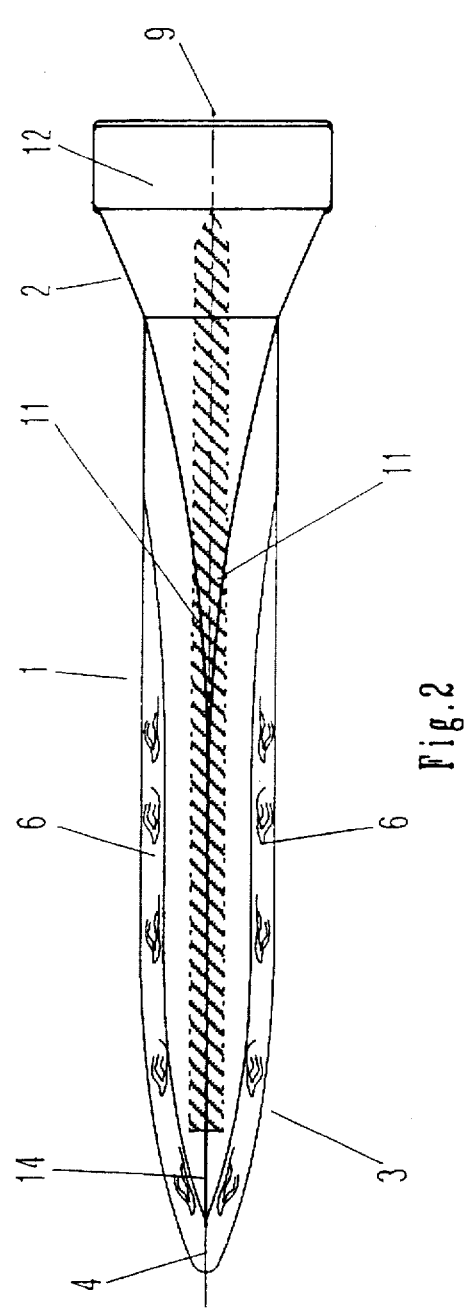

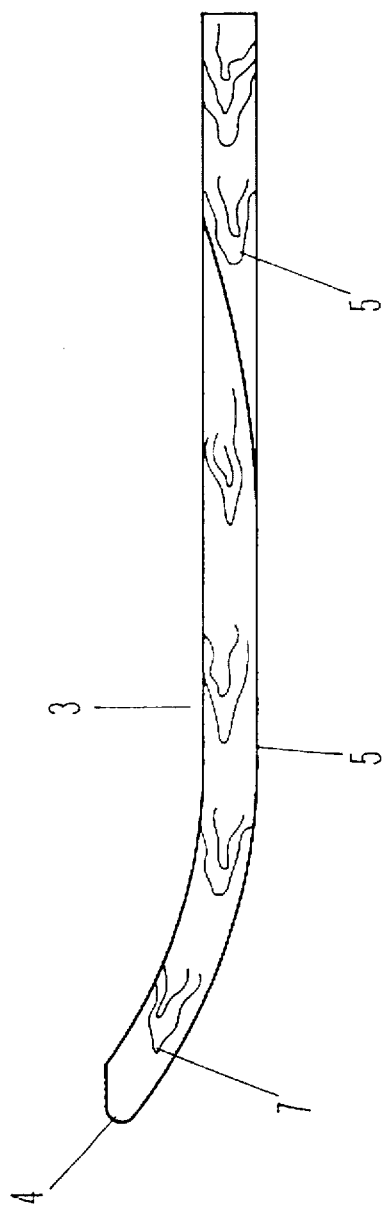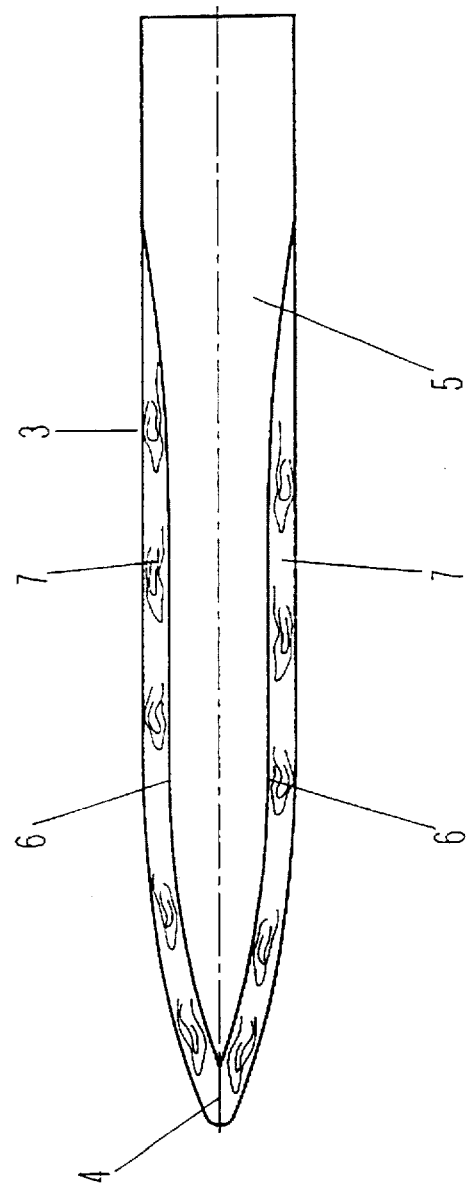

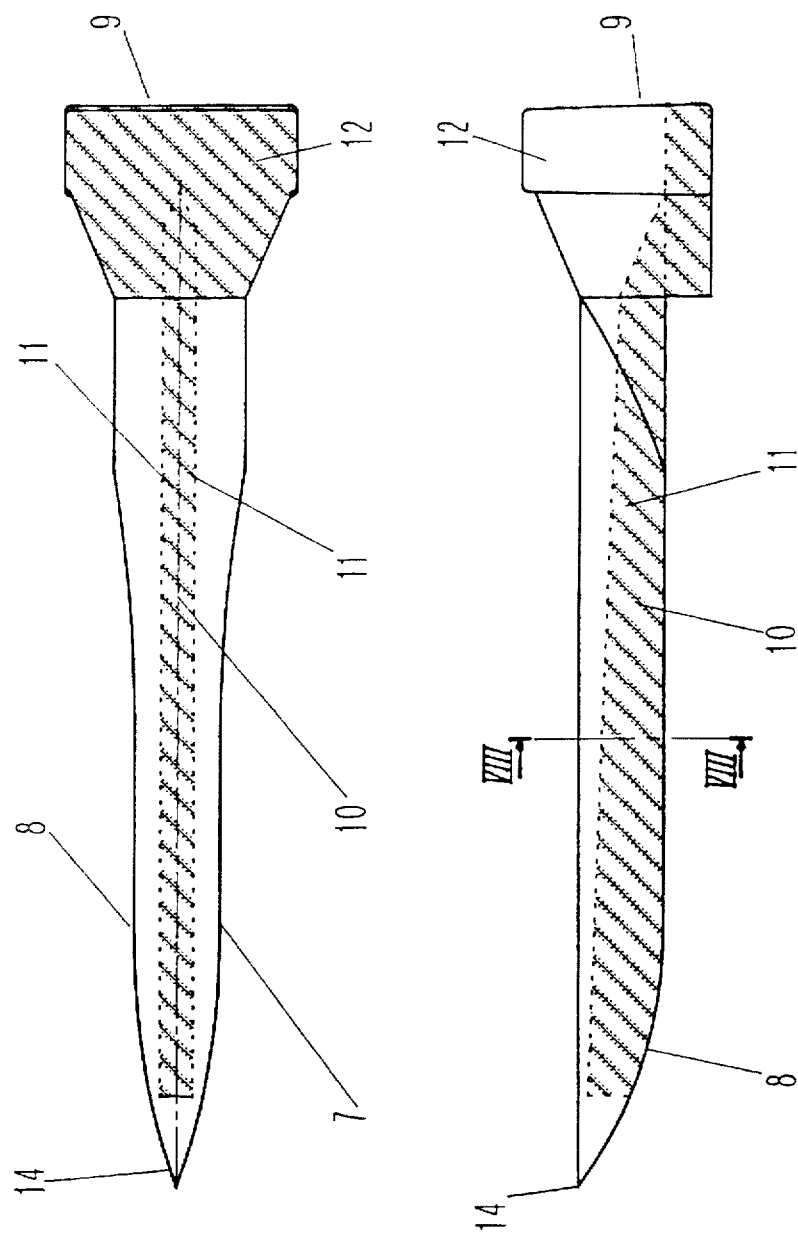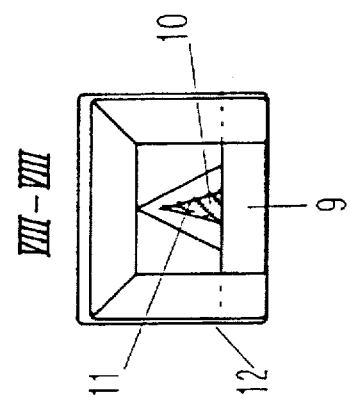

5,743,738

INTERDENTAL WEDGE

BACKGROUND OF THE INVENTION

The present invention belongs to the field of dentistry and dental surgery. It is related to an interdental wedge which is especially useful when approximal fillings of light curing materials are to be inserted into tooth cavities.

BRIEF DESCRIPTION OF THE PRIOR ART

Such a wedge has become known from the European Patent No. EP-B-0,169,803 to the same Applicant, that wedge being made of plastics and containing light conducting elements in order to transmit light necessary for the curing of the fillings that are composed of light sensible synthetic materials to the curing site, and to press the synthetic matrix, i.e. a ribbon of synthetic material, against the tooth in such a manner that the matrix can follow the contours of the tooth. This wedge which is integrally made of plastics is capable of conducting the light to the curing sites; however, the plastics material is not able to press the matrix in a correctly shaped manner against the tooth under treatment, and furthermore, the wedges have the tendency to slip out of the tooth interstices and are therefore not always capable of sufficiently separating the teeth.

In order to achieve a more snugly adapting of the matrix and to prevent a slipping out of the wedge, the document EP-A-0,594,535 to the present Applicant suggests to combine the wedge with a part made of a so-called "memory resin" which can better follow the contours of the tooth. Whereas this embodiment should at least theoretically achieve a good light conduction as well as a good adhesion of the wedge, the practical use has shown an insufficient teeth separating force of the memory resin.

Still other plastics wedges are known where it has been tried to achieve a good adhesion thereof between the teeth; for example, one wedge is disclosed having an inner core of a harder material which is pushed into the inserted wedge; however, the adhesion could not be enhanced to a substantial extent.

Wooden wedges have already been used before the use of plastics wedges, and these wedges have the advantages to well adhere between the teeth and to achieve sufficiently high separation forces. Such wooden wedges can be used for amalgam fillings since these fillings do not need light for hardening. On the other hand, wooden wedges cannot be used for synthetic fillings which need light for curing since wood does not conduct light.

Therefore, the object of the present invention is to provide an interdental wedge which adheres well between the teeth where it is inserted and closely follows the contours of the tooth to be treated, and which is further able to conduct the light necessary for the curing of the filling material to the correct sites. A further object of the invention is to provide such an interdental wedge that is able to achieve sufficiently high teeth separating forces.

SUMMARY OF THE INVENTION

The new interdental wedge according to the present invention comprises the combination of a compressible sole portion and an insert of synthetic material. The insert is arranged on the top of the sole portion. This sole portion is made of a material that is compressible from an uncompressed state under the influence of a force which raises more than proportionally with respect to the compression; this feature allows to achieve a high separation force.

Further objects, features and advantages of the present invention will be disclosed and discussed in the description of special or preferred embodiments of the invention. Reference is made in this respect to the accompanying drawings.

BRIEF DESCRIPTION OF THE DRAWINGS

In the drawings:

FIG. 1 shows a side elevation of the interdental wedge of this invention,

FIG. 2 shows a top view of the wedge of FIG. 1,

FIG. 3 shows a front view of the wedge of FIG. 2 in the direction to the vertex of the wedge, FIGS. 4 and 5 show a side elevation and a top view, respectively, of the wooden sole portion of the wedge according to FIGS. 1 and 2, FIG. 6 shows a view from below of the plastics insert of the wedge of FIG. 1, FIG. 7 shows a side elevation of the plastics insert of the wedge according to FIG. 1, FIG. 8 shows a sectional view according to line VIII—VIII in FIG. 6.

DETAILED DESCRIPTION OF THE INVENTION

Figure 9:
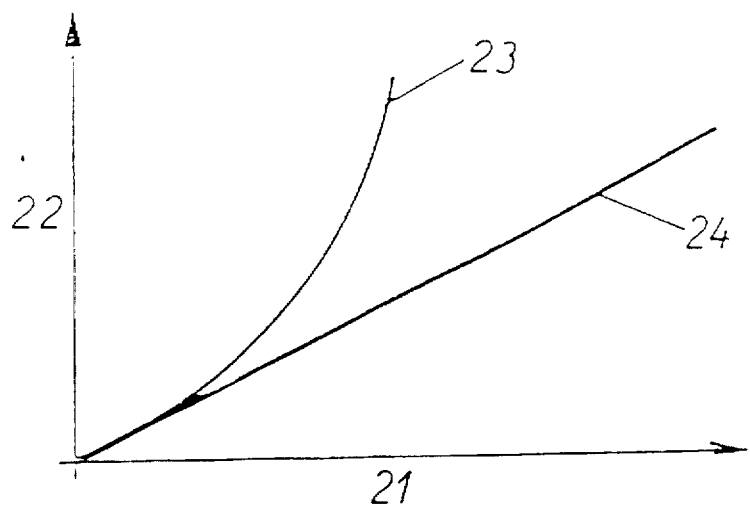
FIG. 9 shows a diagram of the wedge deformation on the abscissa 21 against the applied force on the ordinate 22 for different materials.

In the following, a special and preferred embodiment of the invention will now be described as an Example for a better understanding of the invention. This example will not limit the invention to what will be explained.

Regarding the working and the applications of an interdental wedge having light conducting properties, reference is made to the disclosures of the above mentioned.

The wedge 1 essentially consists of a light conducting plastics insert 2 and a sole portion 3 of wood. The sole portion 3, made of an appropriate wood, known since a long time and having well investigated and known properties, does not only bring about a good and close fitting of the plastics matrix to the contours of the tooth under treatment with the filling to be applied, but also a good adhesion of the wedge between the teeth so that it will not loosen during manipulations, such as the filling of the hole in the tooth by the dentist, and it remains capable of achieving sufficiently high separating forces. The wooden sole portion 3 is bent upward at the top region, see the side elevation of FIG. 4, has a rounded tip portion 4 and comprises essentially a base 5 whose flanks approximately in the foremost third part are running together in a wedge-like manner. The beveled sides 7 of the base 5 are not prolonged until the rearward end, see FIGS. 4 and 5. The borders 6 and the sides 7 of the base are slanted with respect to the base plane against the central axis in order to exert a wedge action in this plane too.

The insert 2 consists of a light conducting synthetic material such as transparent thermoplastic resins, e.g. acrylics, polystyrene or similar, appropriate resins. The undersurface of the tapered front portion 8 is adapted to the arcuated inner shape of the wooden base for being received therein. The insert has a prismatic section whereas the front portion is tapered, viewed from above. The rear end 9 which is opposed to the tip 14 is cuboid shaped, tapered at the front and designed for receiving light coming from an apparatus known per se and conducting it forward.

The plastics insert contains an essentially prismatic, elongated light reflector 10 which is to conduct the incoming light to the two prismatic side faces 11 of the plastics insert and thus onto the composition to be cured. To this end, the entry region 12 of this reflector at the rear end 9 is shaped in a manner to collect as much light as possible and to conduct it onto the prismatic reflector surfaces 11 from where it is then transmitted to the interdental surfaces.

For the manufacture of the interdental wedge of the invention, two methods among others can be used: First, the wooden base is manufactured and inserted into an injection mold, the reflector is fastened on the base, and the parts are inserted into another mold where the plastics insert is mold by injection or casting. According to another method, the wooden base and the insert with the reflector are manufactured separately, and these two parts are connected together by ultrasonic welding, friction welding or by means of an appropriate cement.

Besides wood, other appropriate materials may be used for making the base, under the condition that the base material further presents a compression characteristic similar to that of wood in that wood is rather easily compressible and ductile across the direction of its fibers. Thus, it is further preferred that the wood for making the base is cut in such a manner that the fibers are running in lengthwise direction of the wedge.

However, the force that hinders further deformation is growing rapidly as it is shown in FIG. 9. The abscissa 21 represents the deformation degree, and the ordinate 22 the force which is applied. The curve 23 shows the behavior of wood where the rapidly increasing force necessary for a further deformation or compression can readily be seen. The curve 24 shows for comparison purposes the behavior of an (idealized) elastomer where the force is proportional to the deformation.

The deformation or compression is defined herein as a volume change referring to the starting, uncompressed condition ($\Delta V/V$). The increase of the compression force for obtaining a greater compression must therefore be more than proportional, i.e. the approximation by a polynomial yields, at least in the compression region relevant in practice, powers of more than 1, and preferably of the 2nd degree at least. The region relevant in practice begins with the uncompressed material and ends substantially at the point where the compression force is about equal to the minimal separation force of two adjacent teeth.

Current and typical elastomers as well as other, currently used synthetics are therefore not appropriate according to the experiences made until now. However, it has been found that it is possible to provide thermoplastics or, more preferably, thermoplastic elastomers, with a deformation behavior which is sufficiently similar to that of wood, at least regarding interdental wedges. In order to achieve this conception, it has been found that compressible bodies such as fibers having a high air content, or even gas bubbles, are incorporated into the synthetics material. Examples of such compressible bodies are wood flour, wood fibers, wood chips, wood splints, cellulose fibers, foamed plastics particles, threads, for example of cotton, or fine tubes. A further filler material are liquid crystal polymers (LCP).

In order to obtain a uniform behavior of the base, the inclusion material should be small compared with the dimensions of the base. It is preferred that the included particles have an elongated shape and are more preferably aligned in the lengthwise direction of the new interdental wedge. Also in the case of LCP's, an orientation in lengthwise direction is advantageous. The particles and gas bubbles have preferably sizes in the micrometer range. As an average (number average), values of up to 250 μm in length and 30 μm in thickness, preferably up to 100 μm in length and 10 μm in thickness are considered to be especially useful.

It has also been found that thermoplastic elastomers are superior to regular thermoplastics. A reason therefor may be that a material having elastic properties is able to distribute a pressure applied from the exterior more homogeneously to the compressible inclusions which would result in a more uniform compression. It has been shown in practice that the base becomes stiffer when thermoplastic elastomers are used, in turn resulting in higher separation forces. The aptitude of deformation is nevertheless maintained to a desired extent.

Particularly appropriate matrix materials are ethylene vinylacetate copolymers (EVA) and thermoplastic elastomers, e.g. the ELVAX product line (Du Pont de Nemours, Switzerland).

The manufacture of wedges having a base made of synthetic material can be effected in a similar way as the wooden base, i.e. the base is first manufactured, e.g. by injection molding, and the light conducting plastics body and the reflector are mounted in a second step.

An interesting variant is the manufacture in a sole injection mold. The base is first injected and then the plastics insert. A further advantage is that the synthetics used for the base have a better adhesion to the material of the plastics insert.

We claim:

1. Interdental wedge suitable for use on the insertion of approximal fillings of light during synthetic materials into tooth cavities, comprising:

a compressible sole portion having a top portion; and a light-guiding insert of synthetic material arranged on the top portion of the sole portion, the sole portion being made of a material that is compressible from an uncompressed state under the influence of a compressive force which raises more than proportionally with respect to the compression in order to achieve a high separation force.

2. Interdental wedge according to claim 1, wherein said compressive force, relative to the compression that is expressed as the quotient of the volume change and the uncompressed volume of the sole portion, is approximated by a polynomial that contains at least a power of 2.

3. Interdental wedge according to claim 1, wherein the sole portion is made of at least one of wood and a synthetic material, the synthetic material comprising a matrix wherein at least one of gas bubbles and compressible particles of a filler are distributed, the matrix being selected from the group consisting of at least one thermoplastic resin, at least one thermoplastic elastomer, and a mixture thereof, and the filler being a composition comprising at least one material selected from the group consisting of wood, cellulose, foamed synthetic material, natural threads, synthetic threads, natural fiber materials, synthetic fiber materials, tubular particles, and a liquid crystal polymer (LPC).

4. Interdental wedge according to claim 3, wherein the compressible particles are aligned in lengthwise direction of the interdental wedge.

5. Interdental wedge according to claim 3, wherein the synthetic material of the sole portion matrix is ethylene-vinyl acetate (EVA).

6. Interdental wedge according to claim 3, wherein the compressible particles of the filler and the gas bubbles have an average length of up to 250 μm and a thickness of up to 30 μm.

7. Interdental wedge according to claim 6, wherein the compressible particles of the filler and the gas bubbles have an average length of up to 100 μm and a thickness of up to 10 μm.

8. Interdental wedge according to the claim 3 wherein the filler composition has crystals aligned in the lengthwise direction of the interdental wedge.

9. Interdental wedge according to claim 1, wherein the sole portion comprises a bottom with an upwardly bent tip portion, two borders, and side faces, the side faces being tapered away from center with respect to the longitudinal axis and to the plane of the bottom.

10. Interdental wedge according to claim 1, wherein the light-guiding insert has a front portion with a prismatic sectional shape and a cuboid front surface, inclined lateral surfaces, and a reflector with a prismatic sectional shape and with an entry portion disposed at the cuboid front surface in order to collect light impinging on the cuboid front surface and to conduct the light on the inclined lateral surfaces of the light-guiding insert.

11. Process for the manufacture of an interdental wedge according to claim 1, wherein the sole portion is first prepared and put into an injection mold, then a reflector is fastened thereto, the sole portion and the reflector are introduced into a casting mold, and then the light-guiding insert is molded on the sole portion and the reflector.

12. Process for the manufacture of an interdental wedge according to claim 1, wherein the sole portion and the light-guiding insert are manufactured separately, and the sole portion and the light-guiding insert are then combined by welding or cementing.

13. Interdental wedge suitable for use on the insertion of approximal fillings of light curing synthetic materials into tooth cavities, comprising:

a sole portion for a snugly fitting of a matrix to the approximal contour of the tooth under treatment; and an insert disposed on a top of the sole portion and made of a light conducting synthetic material, the insert comprising means for projecting light necessary for curing and impinging on a flat end surface of the interdental wedge on the filling, the sole portion being made of a material that is compressible from an uncompressed state under the influence of a compressive force which raises more than proportionally with respect to the compression in order to achieve a high separation force.

14. Interdental wedge according to claim 13, wherein said compressive force, relative to the compression that is expressed as the quotient of the volume change and the uncompressed volume of the sole portion, is approximated by a polynomial that contains at least a power of 2.

15. Interdental wedge according to claim 13, wherein the sole portion is made of at least one of wood and a synthetic material, the synthetic material comprising a matrix wherein at least one of gas bubbles and compressible particles of a filler are distributed, the matrix being selected from the group consisting of at least one thermoplastic resin, at least one thermoplastic elastomer, and a mixture thereof, and the filler being a composition comprising at least one material selected from the group consisting of wood, cellulose, foamed synthetic material, natural threads, synthetic threads, natural fiber materials, synthetic fiber materials, tubular particles, and a liquid crystal polymer (LPC).

16. Interdental wedge according to the claim 15 wherein the filler composition has crystals aligned in the lengthwise direction of the interdental wedge.

17. Interdental wedge according to claim 13, wherein the compressible particles are aligned in lengthwise direction of the interdental wedge.

18. Interdental wedge according to claim 17, wherein the sole portion is a matrix made of ethylene-vinyl acetate (EVA).

19. Interdental wedge according to claim 17, wherein the compressible particles of the filler and the gas bubbles have an average length of up to 250 μm and a thickness of up to 30 μm.

20. Interdental wedge according to claim 19, wherein the compressible particles of the filler and the gas bubbles have an average length of up to 100 μm and a thickness of up to 10 μm.

21. Interdental wedge according to claim 13, wherein the sole portion comprises a bottom with an upwardly bent tip portion, two borders, and side faces, the side faces being tapered away from center with respect to the longitudinal axis and to the plane of the bottom.

22. Interdental wedge according to claim 13, wherein the insert has a front portion with a prismatic sectional shape and a cuboid front surface, inclined lateral surfaces, and a reflector with a prismatic sectional shape and with an entry portion disposed at the cuboid front surface in order to collect light impinging on the cuboid front surface and to conduct the light on the inclined lateral surfaces of the insert.

23. Process for the manufacture of an interdental wedge according to claim 13, wherein the sole portion is first prepared and put into an injection mold, then a reflector is fastened thereto, the sole portion and the reflector are introduced into a casting mold, and then the insert is molded on the sole portion and the reflector.

24. Process for the manufacture of an interdental wedge according to claim 13, wherein the sole portion and the insert are manufactured separately, and the sole portion and the insert are then combined by welding or cementing.

* * * * *